US010993907B2

(12) United States Patent
Ellervik et al.

(10) Patent No.: US 10,993,907 B2
(45) Date of Patent: May 4, 2021

(54) GLUCONO DELTA-LACTONE FOR TREATMENT OF VAGINAL FUNGAL INFECTIONS

(71) Applicant: GEDEA BIOTECH AB, Lund (SE)

(72) Inventors: Ulf Ellervik, Loddekopinge (SE); Olov Sterner, Malmo (SE); Helena Strevens, Lund (SE); Sophie Manner, Helsingborg (SE)

(73) Assignee: Gedea Biotech AB, Lund (SE)

( * ) Notice: Subject to any disclaimer, the term of this patent is extended or adjusted under 35 U.S.C. 154(b) by 0 days.

(21) Appl. No.: 16/089,194

(22) PCT Filed: Apr. 6, 2017

(86) PCT No.: PCT/EP2017/058268
§ 371 (c)(1),
(2) Date: Sep. 27, 2018

(87) PCT Pub. No.: WO2017/174731
PCT Pub. Date: Oct. 12, 2017

(65) Prior Publication Data
US 2019/0110983 A1 Apr. 18, 2019

(30) Foreign Application Priority Data
Apr. 6, 2016 (SE) .................... 1650467-2

(51) Int. Cl.
*A61K 9/00* (2006.01)
*A61K 9/02* (2006.01)
*A61K 9/20* (2006.01)
*A61K 31/7004* (2006.01)
*A61K 31/4174* (2006.01)
(Continued)

(52) U.S. Cl.
CPC .......... *A61K 9/0036* (2013.01); *A61K 9/0034* (2013.01); *A61K 9/02* (2013.01);
(Continued)

(58) Field of Classification Search
CPC .......... F27B 14/00; F27B 14/061; F27B 3/12; A61K 9/0034; A61K 31/4164; A61K 31/4174; A61K 31/366
See application file for complete search history.

(56) References Cited

U.S. PATENT DOCUMENTS

| 4,234,599 A | 11/1980 | Van Scott et al. |
| 5,385,938 A | 1/1995 | Yu et al. |

(Continued)

FOREIGN PATENT DOCUMENTS

| CN | 1 124 622 A | 6/1996 |
| EP | 2387882 A2 | 11/2011 |

(Continued)

OTHER PUBLICATIONS

Ferris et al., Obstet. Gynecol., 2002, 99, 419-425.
(Continued)

*Primary Examiner* — Jianfeng Song
(74) *Attorney, Agent, or Firm* — Dinsmore & Shohl LLP; Weston R. Gould

(57) ABSTRACT

The present invention relates to a pharmaceutical formulation for vaginal administration, wherein the formulation comprises a pharmaceutical acceptable excipient and glucono δ-lactone, wherein the glucono δ-lactone is present in an amount of 5 to 99 wt % of the formulation. The invention also relates to a pharmaceutical formulation according to the invention for use in the prevention or treatment of a urogenital fungal infection. Furthermore, the invention relates to glucono δ-lactone (formula (III)), for use in the in the prevention or treatment of a fungal infection.

11 Claims, 5 Drawing Sheets

(51) Int. Cl.
*A61K 31/496* (2006.01)
*A61K 31/4196* (2006.01)
*A61K 31/351* (2006.01)
*A61K 31/513* (2006.01)
*A61K 31/4164* (2006.01)
*A61P 31/10* (2006.01)
*F27D 1/16* (2006.01)
*F27B 14/00* (2006.01)
*F27B 14/10* (2006.01)
*H05B 6/24* (2006.01)
*F27B 14/06* (2006.01)
*F27B 3/12* (2006.01)
*A61K 31/366* (2006.01)
*F27B 14/08* (2006.01)

(52) U.S. Cl.
CPC .............. *A61K 9/20* (2013.01); *A61K 31/351* (2013.01); *A61K 31/366* (2013.01); *A61K 31/4164* (2013.01); *A61K 31/4174* (2013.01); *A61K 31/4196* (2013.01); *A61K 31/496* (2013.01); *A61K 31/513* (2013.01); *A61K 31/7004* (2013.01); *A61P 31/10* (2018.01); *F27B 3/12* (2013.01); *F27B 14/00* (2013.01); *F27B 14/061* (2013.01); *F27B 14/10* (2013.01); *F27D 1/1626* (2013.01); *H05B 6/24* (2013.01); *F27B 2014/066* (2013.01); *F27B 2014/0837* (2013.01)

(56) References Cited

U.S. PATENT DOCUMENTS

| 5,942,250 | A | 8/1999 | Yu et al. |
| 6,541,034 | B1 | 4/2003 | Gergely et al. |
| 9,968,591 | B2 | 5/2018 | Masuda et al. |
| 2003/0017207 | A1* | 1/2003 | Lin ................... A61K 9/0034 424/486 |
| 2004/0126369 | A1* | 7/2004 | Payne ................. A61K 45/06 424/94.4 |
| 2006/0172007 | A1* | 8/2006 | Ahmad ............... A61K 9/0034 424/487 |
| 2007/0059278 | A1 | 3/2007 | Ahmad et al. |

FOREIGN PATENT DOCUMENTS

| JP | 2004529935 A | 9/2004 |
| JP | 2007077152 A | 3/2007 |
| WO | 99/66904 A1 | 12/1999 |
| WO | 00/44230 A1 | 8/2000 |
| WO | 2002/087570 A1 | 11/2002 |
| WO | 2004/014416 A1 | 2/2004 |
| WO | 2008/071783 A1 | 6/2008 |
| WO | 2008/119518 A1 | 10/2008 |
| WO | 2015/143399 A1 | 9/2015 |

OTHER PUBLICATIONS

Harriot et al., Microbiology, 2010, 156, 3635-3644.
Kaur et al., Phytochemistry, 2006, 67, 595-604.
Mota et al., Frontiers in Microbiology, 2015, 6, article 919.
Moyes et al., Nature, 2016, 532, 64.
Sobel, Lancet, 2007, 369, 1961-1971.
Kikuchi pond Wise, Juntendo University School of Medicine Infection Control Science. Education Series: Deep-seated mycosis. "Rare systemic mycosis. (1) Rare yeast-like fungal systemic infection". Med. Mycol. J., vol. 51, pp. 11-18, 2013.
Sashihara; "Bacterial Behavior and Control under Acidic Conditions". Jpn. J. Food Microbic!. 26(2), pp. 81-85, 2009.

* cited by examiner

GLUCONO DELTA-LACTONE FOR TREATMENT OF VAGINAL FUNGAL INFECTIONS

FIELD OF THE INVENTION

The present invention relates to pharmaceutical formulations for vaginal administration for use in treating vaginal fungal infections. Especially, the present invention relates to pharmaceutical formulations for vaginal administration for use in treating vulvovaginal candidosis.

BACKGROUND

The vaginal microbiome is a dynamic system with a complex mixture of various microorganisms in different ratios and quantities, which depends upon lactic acid producing bacteria to maintain a weakly acidic environment (typically pH 3.5 to 4.5). Any sudden change in the vaginal micro-flora will increase the vaginal pH and consequently create a more favorable environment for the establishment of vaginal pathogens, which grow optimally at pH over 5. The imbalance in the flora of microorganisms in the vagina can thus lead to vaginal infections, a condition that affects a large percentage of women of reproductive age each year.

Vaginal *Candida* infection is a common problem, affecting most women at times (more than 75%), but posing a larger and extremely bothersome as well as recurrent problem for a number of women (8%). Symptoms include itching, soreness or irritation, reddened and swollen vaginal tissues, pain with urination and intercourse, typically adhesive white and clumpy curd-like discharge (like cottage cheese) or normal to thin and watery discharge. *Candida albicans* is the most common pathogen, often present in smaller amounts normally in the vagina, mouth, digestive tract and on the skin without causing infection, but with changes in the normal flora, such as after antibiotic treatment, *Candida* can overgrow and infect. However, the knowledge of the occurrence of vulvovaginal infections is to a large degree incomplete due to the psychosocial stigma associated with genital infections.

The virulence of *C. albicans* is mediated by a transformation from planktonic cells into hyphae. The hyphal form, i.e. filamentous cells, has the ability to invade tissue and induce inflammation, mediated by candidalysin, a cytotoxic peptide toxin that destroy the epithelial cells of the vagina (Moyes et. al., Nature, 2016, 532, 64).

*Candida* thrives on the glycogen present in vaginal mucosa, and infection is also facilitated by the effect on the mucosa of increased estrogen levels during pregnancy, and also by the weakened immune system during gestation. Contraceptive pills can cause a similar effect, as can menstruation, as well as other stress factors. Diabetes is another common facilitator.

The diagnosis is established after a vaginal examination with swabbing of the vagina, to obtain a sample of the discharge, on which to perform microscopy of the so-called wet smear or wet mount, with an addition of KOH to lysate the epithelial cells and visualize the *Candida* hyphae. In women with recurrent or persistent symptoms, vaginal cultures should be obtained, as the less common species of *Candida*, such as *Candida glabrata* or *Candida krusei*, require different medications. Self-diagnosis may not be advisable, only 11% of women accurately diagnosed their infection in one study; and women with a previous infection were only slightly more accurate (35%) giving rise to costly treatment with potential adverse effects [D. G. Ferris, et al. Obstet. Gynecol. 2002, 99, 419-425].

Treatments include vaginal creams or tablets such as econazol, clomitrazol, miconazole, tioconazole or butoconazol for 1-3 days or 7-14 days with a persistent condition, although fluconazole is often recommended in a persistent or recurrent infection. Fluconazole can also be given weekly or every other week for 3-6 months, to prevent a recurrent infection. However, though side effects of fluconazole are mild and infrequent, they may include stomach upset, headache and rash. Fluconazole interacts with a number of medications and is not recommended during pregnancy due to the potential risk of harm to the fetus. A resistance to the drug may develop, in which case itrakonazol can be used, but also not during gestation.

Although vulvovaginal candidosis is normally not life threatening, it can be more or less chronic and reduces the quality of life, sex life, work and the ability to concentrate; it can eventually lead to depressions. A chronic condition can cause debilitating vestibulitis, which can be exceedingly difficult to treat. There is evidence supporting that excessive inflammation through prostaglandin production can cause premature contractions and preterm birth. The preterm neonate can subsequently face invasive *Candida* infection, one of the most serious nosocomial infections causing higher morbidity and mortality than bacterial infection, in particular in neonatal intensive care units.

There are growing concerns regarding increasing prevalence of antifungal resistance even with intravenous echincandin treatment. Treatment for women-specific diseases is a relatively underdeveloped area and vulvovaginal infections pose a large and partially hidden problem without effective treatment. Particularly at risk are diabetics and in particular pregnant diabetics. A harmless treatment for use during pregnancy could prove most valuable in prevention also of preterm birth.

Alternative suggested treatments of vulvovaginal candidosis involve use of lactic acid (cf. WO 2008/119518) and lactic acid bacteria (cf. WO 2008/071783), for long having been used in the treatment of bacterial vaginosis. Lactic acid is however far less effective in affecting vulvovaginal candidosis.

As recognized in the art, vulvovaginal candidosis thus remains a common problem worldwide, affecting all strata of society, despite therapeutic advances [J. D. Sobel. Lancet, 2007, 369, 1961-1971].

There is thus a need for new pharmaceutical formulations against vulvovaginal candidosis. The present invention seeks to provide a simple, inexpensive, environmentally friendly solution to the problem with vulvovaginal infections.

SUMMARY

Consequently, the present invention seeks to mitigate, alleviate, eliminate or circumvent one or more of the above-identified deficiencies in the art and disadvantages singly or in any combination by providing a pharmaceutical formulation for vaginal administration, wherein the formulation comprises a pharmaceutical acceptable excipient and glucono δ-lactone (formula (III)),

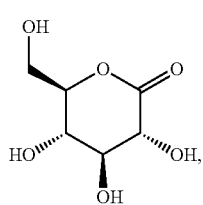

wherein the glucono δ-lactone is present in an amount of 5 to 99 wt % (weight/weight) of the formulation. It has been shown that such a composition reduces the presence of biofilm of different *Candida* species and, additionally also has a cytotoxic effect on several *Candida* species. Glucono δ-lactone (GDA) is a solid at room temperature and at body temperature and is therefore suitable to use as the active ingredient in e.g. a vaginal tablet, disc or suppository or a vagitorium.

According to one embodiment, the glucono δ-lactone is present in an amount of 10 to 70 wt % of the formulation. The glucono δ-lactone may be present in an amount of 20 to 70 wt % of the formulation. The glucono δ-lactone may be present in an amount of more than 50 wt %, such as more than 60 wt %, such as more than 70 wt %, such as more than 75 wt %, such as more than 80 wt %. Such a composition has the advantage of a fast release of an effective dose of glucono δ-lactone.

According to another embodiment, the composition comprises no more than 10 wt % water, preferably no more than 5 wt %. Such a composition has the advantage of long shelf-life and protects the glucono δ-lactone from hydrolysis.

According to one embodiment, the pharmaceutical formulation further comprises an antifungal agent selected from the group consisting of miconazole, terconazole, isoconazole, fenticonazole, fluconazole, nystatin, ketoconazole, clotrimazole, butoconazole, econazole, tioconazole, itraconazole, 5-fluoracil, and metronidazole. Such a composition has the advantage that it is effective in cases were the infection is caused not only by a species which is susceptible to glucono δ-lactone, but has to be treated using another antifungal agent.

According to one embodiment, the pharmaceutical formulation comprises a carrier, a filler, and/or a buffering or pH-adjusting agent.

According to another embodiment, the pharmaceutical formulation is formulated to release a compound according to formula (III) over an extended period of time, such as over at least 4 hours, over at least 6 hours, over at least 8 hours, or over at least 24 hours after administration, such as intravaginal insertion. This has the advantage that the effect of the treatment is prolonged. Further the time intervals between administrations of the composition can be prolonged.

According to yet another embodiment, the pharmaceutical formulation is formulated as a tampon, vagitorium, vaginal aerosol, vaginal cup, vaginal gel, vaginal insert, vaginal patch, vaginal ring, vaginal sponge, vaginal suppository, vaginal cream, vaginal emulsion, vaginal foam, vaginal lotion, vaginal ointment, vaginal powder, vaginal shampoo, vaginal solution, vaginal spray, vaginal suspension, vaginal tablet, vaginal rod, vaginal disc, vaginal device, and any combination thereof, or wherein the pharmaceutical formulation is present on a sanitary article, such as a tampon, a sanitary napkin, an incontinence pad or diaper, or a panty liner.

According to another embodiment, the pharmaceutical formulation is formulated as a vagitorium, vaginal insert, vaginal ring, vaginal suppository, vaginal tablet, vaginal rod, or vaginal disc.

According to one embodiment, the pharmaceutical formulation has the ability to reduce or prevent biofilm formation by *Candida* species. A biofilm is a group of microorganisms in which cells are attached to each other. Often these cells adhere to a surface, such as a mucosal surface. The microbial cells growing in a biofilm are physiologically different from so called planktonic cells of the same organism, which are single-cells that may float or swim in a liquid medium. *Candida* species have the ability to form biofilms. When the biofilm formation is reduced or prevented the individual *Candida* cells can no longer attach to the mucosa of e.g. the vagina. Hence, the further infection is prevented and the *Candida* cells which no longer form a biofilm are discarded from e.g. the vagina.

According to a second aspect of the invention, a pharmaceutical formulation according to the above for use in the prevention or treatment of a urogenital fungal infection is provided.

The glucono δ-lactone may be present as an active ingredient in the pharmaceutical formulation.

According to one embodiment, the urogenital fungal infection is vulvovaginal fungal infection.

According to another embodiment, the urogenital fungal infection is vulvovaginal candidosis.

According to yet another embodiment, the vulvovaginal candidosis is caused by *Candida albicans, Candida glabrata, Candida krusei* and/or *Candida tropicalis*.

According to a third aspect of the invention, glucono δ-lactone (formula (III)),

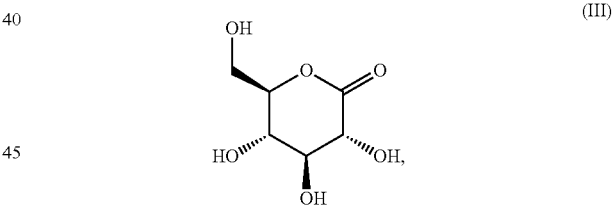

for use in the in the prevention or treatment of a fungal infection is provided.

According to one embodiment, the fungal infection is a urogenital fungal infection.

According to one embodiment, the urogenital fungal infection is vulvovaginal candidosis.

According to another embodiment, the vulvovaginal candidosis is caused by *Candida albicans, Candida glabrata, Candida krusei* and/or *Candida tropicalis*.

Further, advantageous features of various embodiments of the invention are defined in the dependent claims and within the detailed description below.

DETAILED DESCRIPTION OF THE INVENTION

It is estimated that approximately 80% of pathogen infection in humans are related with the formation of biofilm, i.e. the formation of a complex three-dimensional structure of the pathogen bound to cell walls as well as to other pathogen cells. It has been shown that biofilm formation is required for vulvovaginal *Candida* infections [M. M. Harriott, E. A. Lilly, T. E. Rodriguez, P. L. Fidel, M. C. Noverr, Microbiology, 2010, 156, 3635-3644]. Further, the formation of biofilm also reduces the efficiency of anti-fungals by 10-100 times.

Given the importance of formation of biofilm in vulvovaginal *Candida* infections, a biofilm assay was deemed appropriate to evaluate the effect of hydroxylated carboxylic acid in targeting vulvovaginal *Candida* infections. In accordance with reports in the art, lactic acid was found to be moderately active in targeting vulvovaginal *Candida* infections in a biofilm assay (cf. the experimental part below). As biofilm formation is dependent on both pH and the occurrence of alternative carbohydrate sources, it was not surprising to learn that lactic acid provides some effect on the formation of biofilm. Further, also some other hydroxylated C2-C5 carboxylic acids provided similar effects. Their effect is deemed to be related to their acidifying effect, as the stronger acid provided somewhat stronger effects.

Surprisingly it was found that polyhydroxylated C6 carboxylic acids, e.g. gluconic acid, provided superior effects in decreasing formation of biofilm, compared to the closely related C3 and C5 analogs (i.e. glyceric acid and xylonic acid, respectively). Even more surprising, polyhydroxylated C6 carboxylic acid, e.g. gluconic acid, was found to be superior also compared to the more acidic hydroxylated carboxylic acids, such as citric acid.

Whereas the effect of other hydroxylated carboxylic acids seemingly only is due to their acidity (lowering the pH hampers the formation of biofilm), the effect of polyhydroxylated C6 carboxylic acids, e.g. gluconic acid, on formation of biofilm is pronounced already at pH<7. Thus, it seems that the effect of polyhydroxylated C6 carboxylic acid, e.g. gluconic acid, on formation of biofilm not merely is related to its acidity, but the compound itself, or more precisely the related δ-lactone thereof, also provides an effect.

In the art, D-gluconic acid produced by the *Pseudomonas* strain AN5 has been demonstrated to have an effect on the take-all disease of wheat caused by the fungus *Gaeumannomyces graminis* var. *tritici* (R. Kaur et. al., Phytochemistry 67 (2006) 595-604; see also WO 00/44230 A1). The authors suggest that the ability of D-gluconic acid and other antifungal agents produced by *Pseudomonas* strains, e.g. phenanzine-1-carboxylic acid (PCA) and 2,4-diacetylphloroglucinol (DPG), to inhibit the take-all fungus must be, at least in part, due to their ability to lower pH in the wheat rhizosphere.

Without being bond by any theory, it may be that presence of gluconic acid favors planctonic cells over biofilm formation *candida* species, as polyhydroxylated C6 carboxylic acid, e.g. gluconic acid, may be used by *candida* species and other eucaryotes in the pentose phosphate pathway.

In water solution gluconic acid (GA, CAS 526-95-4) is in equilibrium with the glucono-δ-lactone (GDA, CAS 90-8-2) and the glucono-γ-lactone (GGA). Gluconic acid is difficult to produce as a solid crystalline product and is usually supplied as a 50% water solution.

Whereas such a water solution may be used to provide a liquid pharmaceutical formulation for vaginal administration, such as a vaginal cream, a vaginal gel, the water solution is less suitable for use in providing a solid pharmaceutical formulation for vaginal administration, such as a vaginal tablet, a vaginal suppository, or a vaginal ring.

To solve this problem, the inventors investigated the possibility to use glucono-δ-lactone (GDA) in the preparation of solid pharmaceutical formulations. Surprisingly, the inventors found that GDA as such, i.e. the lactone itself, has an effect on the formation of biofilm of different *Candida*-species. Further studies revealed that the effect of GDA on biofilm formation and viability of *Candida* species is in comparison with the effect of gluconic acid, implicating that GDA in itself acts as an active compound.

An embodiment of the invention thus relates to pharmaceutical formulation for vaginal administration comprising a compound according to formula (III), being glucono-δ-lactone (GDA).

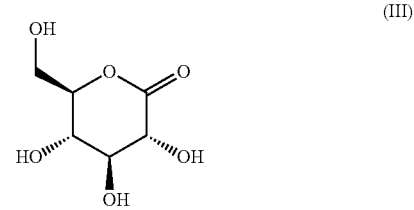 [SMILES: O=C1O[C@H](CO)[C@@H](O)[C@H](O)[C@H]1O]

(III)

Further the pharmaceutical formulation comprises a pharmaceutical acceptable excipient to provide a formulation. In this context "pharmaceutically acceptable" means an excipient that, at the dosage and concentration employed, does not cause any unwanted effects in the subjects to whom it is administered. Such pharmaceutically acceptable excipients are well-known in the art. They may be selected from the group consisting of carriers, diluents, binders, disintegrating agents, flow-improving agents, pH-adjusting agents, stabilizing agents, viscosity adjusting agents, preservatives, gelling or swelling agents, surfactants, emulsifying agents, suspending agents, bases for suppositories, vagitories or pessaries, bases for creams, ointments, gels, lotions, shampoos, foam, sprays and the like. As recognized by the skilled person, the specific choice of pharmaceutically acceptable excipients depends on the specific form or the formulation, e.g. the dosage form. A person skilled in the art can find guidance in various textbooks, e.g. Remington: The Science and Practice of Pharmacy, in providing suitable pharmaceutically acceptable excipients. Such a pharmaceutical formulation is useful in the treatment and/or prevention of vulvovaginal fungal infections.

The pharmaceutically acceptable excipient may be a lipophilic or hydrophilic carrier. Examples of lipophilic carriers are waxes, oils, isopropyl myristate, solid triglycerides, and cocoa butter. Examples of hydrophilic carriers are glycerol, propylene glycol, and polyoxyethylene glycol.

Further, the excipient may be a filler. Examples of fillers include saccharides, such as lactose, maltose and trehalose. Other disaccharides like e.g. sucrose, lactulose, cellobiose etc. may also be suitable for use in the present context. In a composition of the invention, a disaccharide normally contributes to a suitable structure of the composition. Saccharides may also serve as lyophilization aid.

In aqueous solution, compounds according to formula (I) are in equilibrium with corresponding lactones, e.g. δ-lactone and γ-lactone.

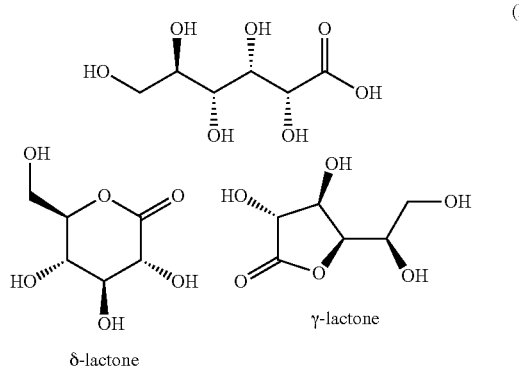

The active ingredient of the pharmaceutical formulation may thus comprise a small amount of the acid (cf. formula (I)) and/or glucono-γ-lactone.

According to an embodiment, the compound according to formula (III) is partly present in the pharmaceutical formulation as an acid (formula (I)) in its non-charged protonated form, e.g. gluconic acid, and partly as the corresponding addition salt, i.e. a conjugate base, e.g. gluconate. Thus, the gluconic acid may serve to buffer the pharmaceutical formulation. The ratio between the acid in its non-charged protonated form and the conjugate base may be chosen to provide a suitable pH, such as 3.5 to 4.5, upon administration. The pharmaceutical formulation may thus restore normal physiological pH in the vagina upon administration. However, given the activity of compounds according to formula (III) already at pH 6.5 or lower, the pH must not by necessity be restored for the pharmaceutical formulation to provide is effect. It is however preferred if pharmaceutical formulation provides a pH of 6.0 or less, such as 5.0 or less, upon administration. The pharmaceutical formulation should preferably not provide a pH lower than 3.0, more preferably not lower than 3.5, upon administration.

While the compound according to formula (III) in the form of the corresponding acid in its non-charged protonated form and/or the corresponding addition salt, i.e. a conjugate base, may be used to provide pH modifying properties to the pharmaceutical formulation, the pharmaceutical formulation may comprise additional buffering or pH-adjusting agents. Such buffering or pH-adjusting agents may be pharmaceutically acceptable buffering agents suitable for adjustment of pH to from about 3 to about 5, such as from 3.5 to 4.5. Examples of buffering or pH-adjusting agents include lactic acid, acetic acid, citric acid, malonic acid, phosphoric acid, tartaric acid, maleic acid etc. and their corresponding conjugate bases, i.e. lactate, acetate, citrate, malonate, phosphate, tartrate, and maleate.

Furthermore, the pharmaceutical formulation may also comprise one or several pharmaceutically acceptable salts such as succinate, lysinate, cypionate, valerate, hemisuccinate, butyrate, or trometamol salt alone or in combination.

The pharmaceutical formulation is to comprise a pharmaceutical active amount of a compound according to formula (III). According to a preferred embodiment the pharmaceutical formulation comprises at least 5 wt %, such as at least 10 wt %, 15 wt %, 20 wt %, 25 wt %, 30 wt %, 40 wt %, 50 wt %, 60 wt %, or 75 wt %, of a compound according to formula (III). Further, the pharmaceutical formulation may comprises not more than 99 wt %, such as not more than 95 wt %, 90 wt %, 80 wt %, 75 wt %, 70 wt %, 60 wt %, or 50 wt %, of a compound according to formula (III). Thus, the pharmaceutical formulation may comprise from 5 wt % to 99 wt % of a compound according to formula (III). As recognized be the skilled person, the range may be narrowed based on the upper and lower amounts specified above, such as 10 to 95 wt %, 10 to 80 wt %, 15 to 90 wt %, 20 to 75 wt %, 30 to 70 wt %. The pharmaceutical formulation may comprise between 40 wt % and 90 wt % of a compound according to formula (III). The pharmaceutical formulation may comprise between 50 wt % and 80 wt % of a compound according to formula (III). The pharmaceutical formulation may comprise between 60 wt % and 70 wt % of a compound according to formula (III).

According to another embodiment the pharmaceutical formulation comprises glucono-δ-lactone (III) and optionally, but not necessarily, gluconic acid (I). In such an embodiment, the molar ratio of the glucono-δ-lactone (III) and the gluconic acid (I) in the formulation may be at least 9:1 (III:I), preferably at least 49:1 (III:I), more preferably at least 99:1 (III:I). As the glucono-δ-lactone (III) will be hydrolyzed to the gluconic acid (I), it may be preferred for a high proportion of the glucono-δ-lactone (III) in the pharmaceutical formulation. The pharmaceutical formulation may according to such an embodiment comprise less than 1 wt % of the gluconic acid (I), such as less than 0.1 wt %, 0.05 wt %, 0.01 wt %, 0.005 wt %, or 0.001 wt % of the gluconic acid (I).

Upon vaginal insertion of the pharmaceutical formulation, the lactone will be exposed to aqueous conditions causing hydrolysis. As the hydrolysis will not be instant, the pharmaceutical formulation will release the compound according to formula (III) over an extended period of time, prolonging its effect. In addition the compound according to formula (I) may be released as the free acid or as the conjugate base thereof and thus add a pH-lowering effect. The pH of the vagina may vary between 3.5 and 4.5, and in the case of a fungal or bacterial infection it may rise above 4.5.

Further, as recognized by the skilled person the pharmaceutical formulation may be formulated for extended release, further prolonging the effect. The pharmaceutical formulation may be formulated to release a compound according to formula (III) over an extended period of time, such as over at least 4 hours, over at least 6 hours, over at least 8 hours, or over at least 24 hours, after intravaginal insertion.

Further, glucono-δ-lactone (III) may, apart from acting as active ingredient, act as filler and/or carrier facilitating formulation of a composition comprising glucono-δ-lactone (III) in a pharmaceutical formulation, such as semi-solid or solid pharmaceutical formulation.

Apart from the excipient, the pharmaceutical formulation may comprise an additional antifungal agent. The antifungal agent may be selected from the group consisting of miconazole, terconazole, isoconazole, fenticonazole, fluconazole, nystatin, ketoconazole, clotrimazole, butoconazole, econazole, tioconazole, itraconazole, 5-fluoracil, and metronidazole. The amount of antifungal agent per dose may be in the range from 0.1 mg to 2000 mg. A compound according to formula (III) and such an additional antifungal agent may act in a synergistic manner.

Sometimes, but not always, vulvovaginal fungal infections also involve bacterial infections. Gluconic acid will provide an effect similar to the effect of lactic acid against bacterial infections due to its acidity. Thus, in addition, glucono-δ-lactone (III) may also have an effect on bacterial infections. It may however be preferred to supplement the pharmaceutical formulation with one or more additional antibacterial agents. According to an embodiment, the pharmaceutical formulation thus comprises one or more antibacterial agents. The antibacterial agent may be selected from the group consisting of clindamycin, tetracycline, amoxicillin, ampicillin, erythromycin, doxycycline, lumefloxacin, norfloxacin, afloxam, ciproflaxin, azitromycin, cefltoxine. The amount of antibacterial agent may be in the range from 5 mg to 1000 mg per dose.

Furthermore, the pharmaceutical formulation may comprise one or more pathogen-antiadhesion agents. As already discussed, the vulvovaginal fungal infections involve biofilm formation and adhesion of fungi to the vaginal mucosa. According to an embodiment the pharmaceutical formulation thus comprises one or several antiadhesion agents preventing mucoadhesion by pathogens, e.g. fungi. Antiadhesion agents may be agents that serve as either a barrier preventing adhesion or as an agent that causes already adhered microorganisms to disadhere. Examples of antiadhesion agents causing disadherence may be mannose, lactose, xylitol, and other sugar alcohols.

The pharmaceutical formulation is preferably formulated for administration to the vagina, e.g. intravaginally. According to an embodiment, the pharmaceutical formulation is thus formulated as a tampon, vagitorium, vaginal aerosol, vaginal cup, vaginal gel, vaginal insert, vaginal patch, vaginal ring, vaginal sponge, vaginal suppository, vaginal cream, vaginal emulsion, vaginal foam, vaginal lotion, vaginal ointment, vaginal powder, vaginal shampoo, vaginal solution, vaginal spray, vaginal suspension, vaginal tablet, vaginal rod, vaginal disc, vaginal device, and any combination thereof. Preferably the pharmaceutical formulation is formulated as a vagitorium, vaginal aerosol, vaginal cup, vaginal gel, vaginal ring, vaginal sponge, vaginal suppository, vaginal cream, vaginal emulsion, vaginal foam, vaginal lotion, vaginal ointment, vaginal shampoo, vaginal solution, vaginal spray, vaginal suspension, vaginal tablet, vaginal rod, or vaginal disc; more preferably as a vagitorium, vaginal insert, vaginal ring, vaginal suppository, vaginal tablet, vaginal rod, or vaginal disc. The the pharmaceutical formulation may also be a liquid formulation, such as vaginal aerosol, vaginal gel, vaginal cream, vaginal emulsion, vaginal foam, vaginal lotion, vaginal ointment, vaginal shampoo, vaginal solution, vaginal spray, vaginal suspension, or any combination thereof.

According to alternative, but less preferred embodiment, the pharmaceutical formulation is present on a sanitary article, such as a tampon, a sanitary napkin, an incontinence pad or diaper, or a panty liner.

The pharmaceutical formulation may be further formulated for extended release, i.e. to release a compound according to formula (III) and/or (I) over an extended period of time, such as over at least 4 hours, over at least 6 hours, over at least 8 hours, or over at least 24 hours, after administration, e.g. intravaginal insertion. The compound according to formula (I) may be released as the acid in its non-charged protonated form and/or as the corresponding conjugate base. Further, as already outlined, the formulation may release the glucono δ-lactone in un-hydrolyzed form. By formulating the pharmaceutical formulation for extended release, the pharmaceutical formulation will exert its effect for longer time. This may be beneficial in restoring normal conditions in the vagina and treating and/or preventing vulvovaginal fungal infection.

As already elaborated, a pharmaceutical formulation for vaginal administration comprising a compound according to formula (III)

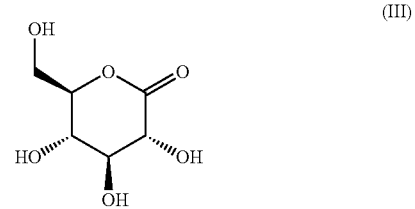 [SMILES: O=C1O[C@H](CO)[C@@H](O)[C@H](O)[C@H]1O]

has the ability to reduce or even prevent formation of biofilm formation by *Candida* species. Further, such pharmaceutical formulations may have the ability to reduce or even dissolve biofilms formed by *Candida* species.

As already elaborated, glucono δ-lactone (III), may thus be used in the prevention or treatment of a urogenital fungal infection, such as a vulvovaginal fungal infection. One embodiment thus relates to the pharmaceutical formulation, as disclosed herein, for use in the prevention or treatment of a urogenital fungal infection, such as a vulvovaginal fungal infection. Typically, the urogenital fungal infection is vulvovaginal candidosis involving infection by *Candida* species, such as *Candida albicans, Candida glabrata, Candida krusei*, and *Candida tropicalis*.

Vulvovaginal candidosis infection is excessive growth of *Candida* in the vagina that causes symptoms associated with inflammation such as itching, soreness or irritation, reddened and swollen vaginal tissues, pain with urination and intercourse, typically adhesive white and clumpy curd-like discharge or normal to thin and watery discharge.

Similarly, one embodiment of the invention relates to use of glucono δ-lactone for the manufacture of pharmaceutical formulation, as disclosed herein, for use in the treatment and/or prevention of a urogenital fungal infection, such as a vulvovaginal fungal infection. Typically, the urogenital fungal infection is vulvovaginal candidosis involving infection by *Candida* species, such as *Candida albicans, Candida glabrata, Candida krusei*, and *Candida tropicalis*.

Yet another embodiment relates to a method of prevention and/or treatment of a urogenital fungal infection, such as a vulvovaginal fungal infection, comprising administering to a mammal, including man, in need of such prevention and/or treatment, a therapeutically effective amount of the pharmaceutical formulation, as disclosed herein. Typically, the urogenital fungal infection is vulvovaginal candidosis involving infection by *Candida* species, such as *Candida albicans, Candida glabrata, Candida krusei*, and *Candida tropicalis*.

A pharmaceutical composition according to embodiments herein may be administered to a patient in a pharmaceutically effective dose. By "pharmaceutically effective dose" is meant a dose that is sufficient to produce the desired effects in relation to the condition for which it is administered. The exact dose may be dependent on the manner of administration, nature and severity of the disorder and/or disease and the general conditions, such as age and body weight of the patient.

According to one embodiment, a pharmaceutical composition as disclosed herein is to be administered at least once daily for at least a week, although other dose regimen may be used as well.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

According to one embodiment treatment does also encompass pre-treatment, i.e. prophylactic treatment.

Although the present invention has been described above with reference to specific illustrative embodiments, it is not intended to be limited to the specific form set forth herein. Any combination of the above mentioned embodiments should be appreciated as being within the scope of the invention. Rather, the invention is limited only by the accompanying claims and other embodiments than the specific above are equally possible within the scope of these appended claims.

In the claims, the term "comprises/comprising" does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. The phrases "at least one" or "one or more" refer to 1 or a number greater than 1, such as to 1, 2, 3, 4, 5, 6, 7, 8, 9, or 10.

MATERIALS AND METHODS

Figure 1:
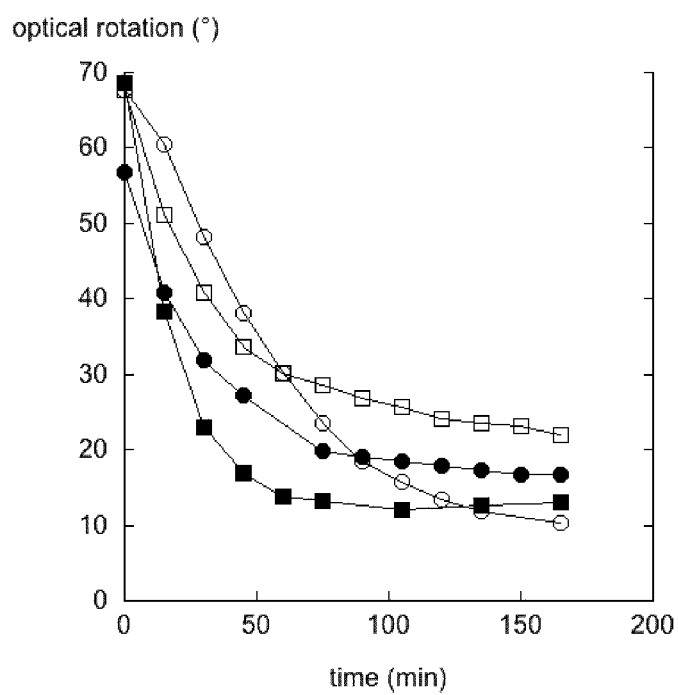
FIG. 1 show changes in optical rotation in the hydrolysis of GDA in distilled water (unfilled circles), pH 4 buffer (filled squares), pH 5 buffer (unfilled squares), and pH 7 buffer (filled circles).

Glucono-δ-Lactone
Solid glucono-δ-lactone (GDA, CAS 90-8-2) was obtained from commercial suppliers.
Biofilm Formation Assay
Yeast strains were grown at 37° C. in complete medium YPD (0.5% (weight/volume) yeast extract, 1% (weight/volume) peptone, 2% (weight/volume) glucose) or minimal medium consisting of YNB (yeast nitrogen base without amino acids and ammonium sulphate, FORMEDIUM™, CYN0505) supplemented with 0.5% (weight/volume) ammonium sulphate, 0.2% (weight/volume) glucose and 100 mM L-proline. If needed 2% (weight/volume) agar was used to solidify media. The liquid minimal medium (YNB (yeast nitrogen base without amino acids and ammonium sulphate, FORMEDIUM™, CYN0505) supplemented with 0.5% ammonium sulphate, 0.2% (weight/volume) glucose and 100 mM L-proline) was used for biofilm assay (biofilm medium).

In the experiments on the impact of pH on biofilm (Example 2 below) the pH values (from 2.6 to 6.6) were obtained using either different potassium phosphate buffers at the final concentration 0.25 M, or by the addition of GDA to the biofilm medium.
Yeast Strains
The strains used in the biofilm formation experiments are described in Table 1.

TABLE 1

Yeast strains used in biofilm experiments.

| Original name | Laboratory strain designation | Description | Reference |
| --- | --- | --- | --- |
| *Candida albicans* SC5314 | Y775 | Wild-type, virulent in a mouse model of systemic infection, sequenced strain | [A. M. Gillum, et al. Mol. Gen. Genet. 1984, 198, 179-182] |
| *Candida glabrata* CBS138 | Y1092 | Wild-type, type strain isolated from human feces, sequenced strain | [B. Dujon, et al. Nature, 2004, 430, 35-44] |

Measurement of Biofilm
Biofilm was measured in liquid culture as described [K. Scherz et al., G3 (Bethesda), 2014, 4, 1671-1680. I. Serrano-Fujarte et al. Biomed Res Int. 2015; 2015: 783639] with some modifications. Prior the biofilm assay, yeast cultures were grown in liquid YPD medium for 24 hours until stationary phase cells were then pelleted by centrifugation (1699×g), washed with sterile water and the cells were further inoculated into test biofilm medium (YNB (yeast nitrogen base without amino acids and ammonium sulphate) supplemented with 0.5% ammonium sulphate, 0.2% glucose and 100 mM L-proline pH7.0) at final concentration of 0.2 $OD_{600}$/ml and incubated in 96-well flat-bottom polystyrene microtiter plates (Sigma Aldrich, Corning® Costar® culture plates, CLS3596-50EA) for 72 hours at 37° C. thermostat. At defined time points crystal violet (HT901-8FOZ; Sigma Aldrich) was added to the media at the final concentration 0.05% In addition, total biomass was measured. After 24 hours of cells staining, plate wells were washed four times with 200 •l of water to remove planktonic cells (cells which are not part of a biofilm), biofilms were then dried and dissolved in 200 •l of 96% ethanol. Total biomass and crystal violet biofilm staining measurements were performed at $OD_{560}$ with FLUOstar OPTIMA plate reader, BMG LABTECH. Crystal violet biofilm measurements were normalized to the total biomass ($OD_{560}$Biofilm/$OD_{560}$ total biomass).

EXAMPLES

Example 1—Hydrolysis of Glucono-δ-Lactone (GDA)

In water solution glucono-δ-lactone (GDA) is in equilibrium with gluconic acid (GA, CAS 526-95-4). GDA (200 mg) was added to distilled $H_2O$ (20 mL), pH 4 buffer, pH 5 buffer, or pH 7 buffer at 37° C. The optical rotation and pH were measured over time. Optical rotation, measured at 37° C., sodium D line, C=10 mg/mL, path length=10 cm. The optical rotation of GDA is approximately 66°. The optical rotation of gluconic acid is approximately 5° [D. T. Sawyer, J. B. Bagger, J. Am. Chem. Soc., 1959, 81, 5302-5306]. This experiment shows that GDA is slowly hydrolyzed to a mixture of GDA and GA (FIG. 1). The equilibrium is pH-dependent and relevant concentrations of GDA are present at all buffered conditions.

Example 2—Biofilm Formation of Candida albicans at Different pH

Figure 2:
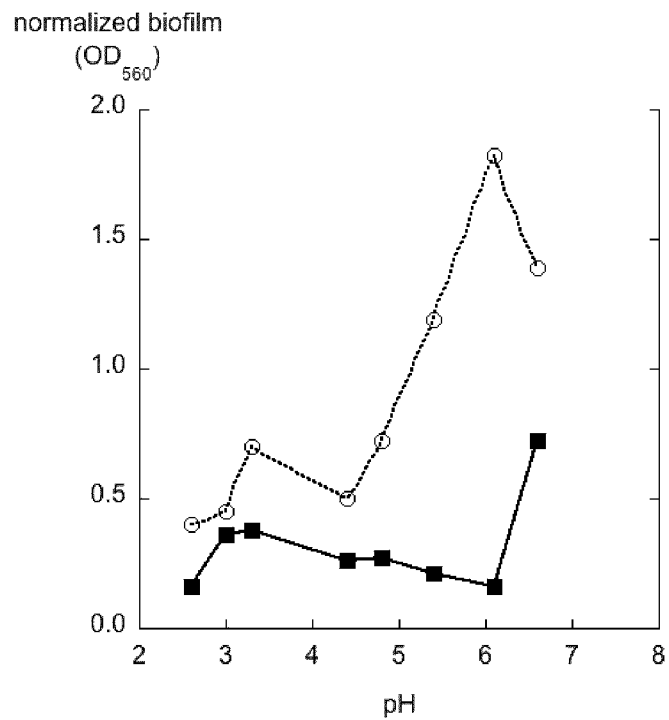
FIG. 2 shows normalized biofilm formation of *Candida albicans* in the minimal media at pH 2.6-6.6 with phosphate buffer (unfilled circles, dotted line) or GDA (filled squares, solid line). The biofilm was measured after 24 h and the staining was performed with crystal violet.

As can be seen from FIG. 2, GDA shows strong effects on the biofilm formation of C. albicans, while the effects from phosphate buffer are much less pronounced. Further, GDA shows strong effect also at pH values up to around at least 6, whereas the effect from buffer are diminished already at pH 5.

Example 3—Biofilm Formation in a Model of In Vivo Conditions Using GDA

Figure 3A:
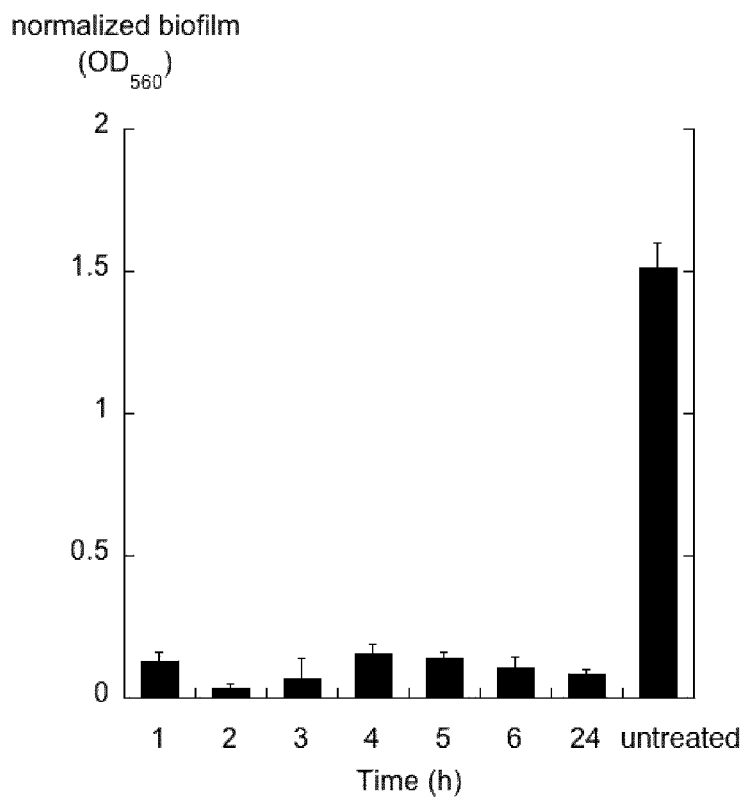
FIG. 3a shows normalized biofilm formation of *Candida albicans* treated with GDA. A pellet of GDA was added to a buffer solution of pH 3.71 (10 mL) at 37° C. Samples (4 mL) were taken after 1, 2, 3, 4, 5, 6 and 24 hours and new buffer solution (4 mL) was added. The samples were diluted 50 times with biofilm medium and the amount of biofilm formation was measured after 24 h.
Figure 3B:
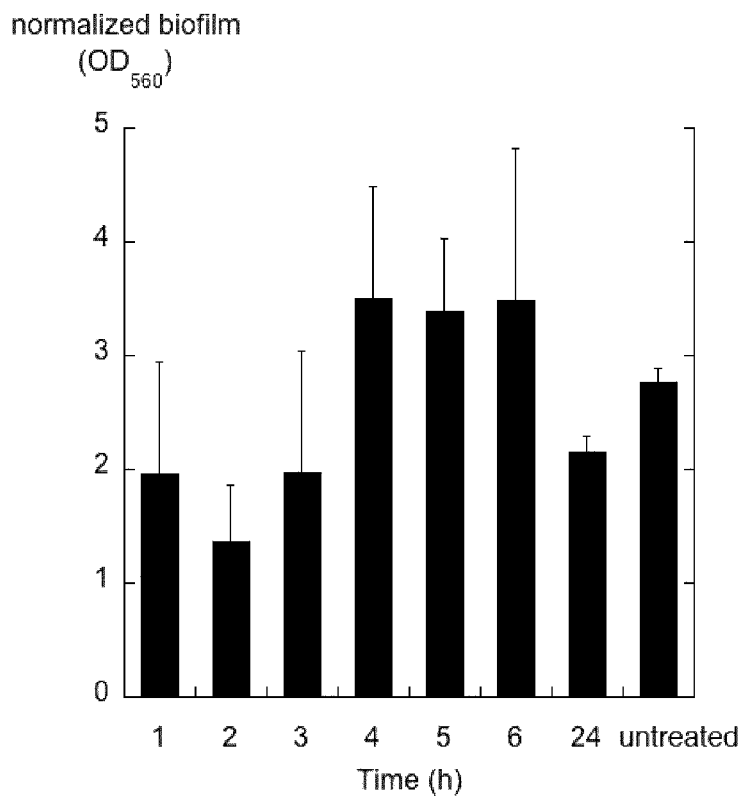
FIG. 3b shows normalized biofilm formation of *Candida glabrata* treated with GDA. A pellet of GDA was added to a buffer solution of pH 3.71 (10 mL) at 37° C. Samples (4 mL) were taken after 1, 2, 3, 4, 5, 6 and 24 hours and new buffer solution (4 mL) was added. The samples were diluted 50 times with biofilm medium and the amount of biofilm formation was measured after 24 h.

Pellets of GDA (2.5 g, duplicate samples) were added to buffer solution of pH 3.71 (0.5 M $KH_2PO_4$/ortho phosphoric acid, 10 mL) at 37° C. Samples (4 mL) were taken at fixed time points (1, 2, 3, 4, 5, 6 and 24 h) and new buffer solution (4 mL) was added. The samples were diluted 50 times with biofilm medium (vide supra) and the amount of biofilm formation was measured after 24 h as described above. As seen from FIG. 3a, the released GDA significantly reduces the amount of biofilm formation in C. albicans. Further, the hydrolysis of the pellet is seemingly slow enough to provide a preventive effect for at least up to 24 hours, likely far more. The effect is less pronounced with C. glabrata (FIG. 3b).

TABLE 2

Biofilm formation of C. albicans and C. glabrata treated with GDA in a model of in vivo conditions. Samples were taken after 1 h, diluted 50 times with biofilm assay medium and the amount of biofilm formation was measured after 24 h.

| | Normalized biofilm (% of control), 1 h |
|---|---|
| Candida albicans | 8.3 |
| Candida glabrata | 71 |

The results show that biofilm formation of both C. albicans and C. glabrata was reduced in the presence of GDA. In addition to diminished biofilm formation, GDA may affect the viability of mature biofilm of C. albicans and C. glabrata.

Example 4—Viability of Mature Biofilms of C. albicans and C. glabrata Treated with GDA Viability of biofilms of C. albicans and C. glabrata after treatment with GDA at different concentration and different time periods was evaluated by staining the cells with XTT. XXT is a colorimetric assay for quantification of cellular viability, and cytotoxicity. The assay is based on the cleavage of the tetrazolium salt XTT, a conversion that only occurs in viable cells. The mature biofilm was exposed to GDA for 24 h. Then the cells were washed 2 times with PBS, after which the XTT reaction mixture was added. After 30 min the optical density measured at 485 nm.

Figure 4A:
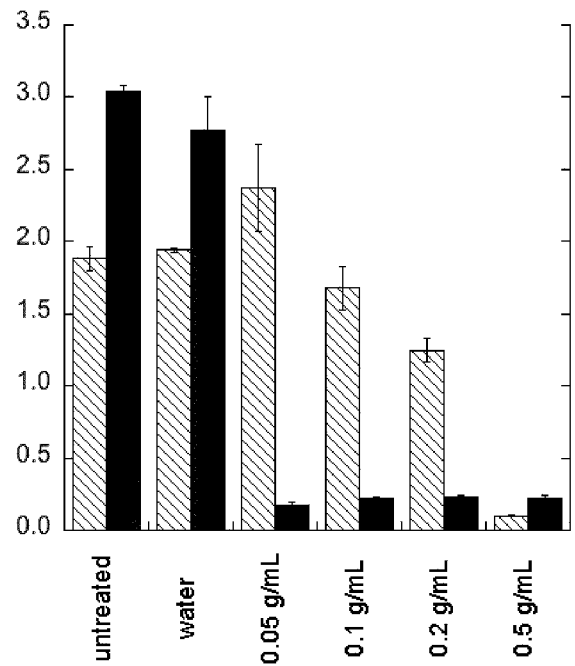
FIG. 4a shows the viability of biofilms of *C. albicans* and *C. glabrata* after treatment with GDA at different concentrations for 24 h. The biofilm staining was performed with XTT. Optical density measured at 485 nm. Diagonal stripes indicate data for *C. albicans*. Filled black columns indicate data for *C. glabrata*.
Figure 4B:
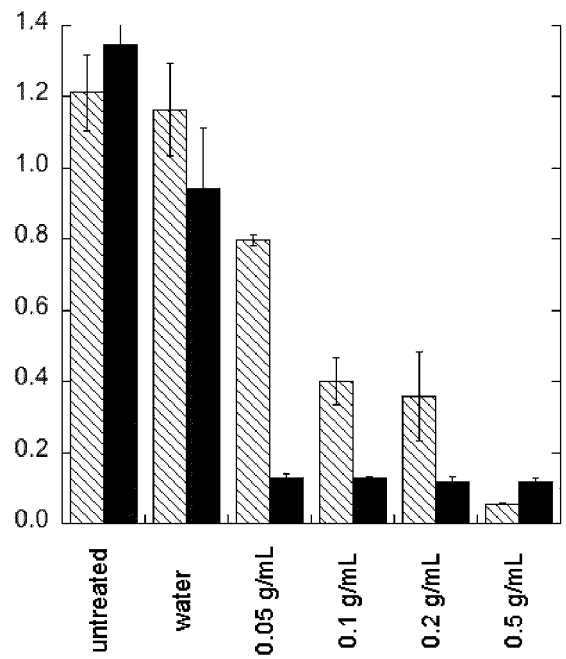
FIG. 4b shows the viability of biofilms of *C. albicans* and *C. glabrata* after treatment with GDA at different concentrations for 48 h. The biofilm staining was performed with XTT. Optical density measured at 485 nm. Diagonal stripes indicate data for *C. albicans*. Filled black columns indicate data for *C. glabrata*.

The XTT assay showed a strong decrease in viability for C. glabrata already after 24 h of incubation (FIG. 4a). The effect was less pronounced for C. albicans but clearly seen after 48 h (FIG. 4b).

Figure 5:
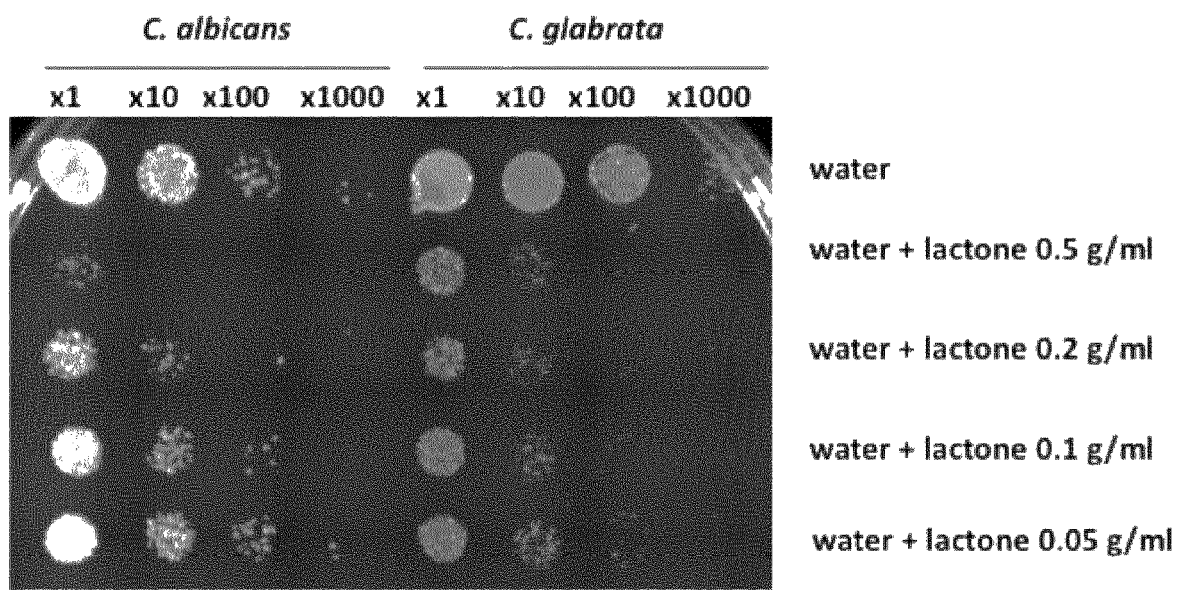
FIG. 5 shows the effect of GDA on mature biofilm of *C. albicans* and *C. glabrata*. Mature biofilm (grown for 48 h) was incubated with GDA for 5 h at 37° C. and then cells at serial dilution were plated on YPD plate to estimate cell survival.

Furthermore, mature biofilm (grown for 48 h in YNB, 0.2% glucose, 100 mM proline) of C. albicans and C. glabrata was incubated with GDA of different concentrations (0.05-0.5 g/ml) at 37° C. For this purpose biofilm medium (YNB, 0.2% glucose, 100 mM proline) was removed and GDA was added, which was dissolved either in water at concentration 0.05, 0.1, 0.2 and 0.5 g/ml. After incubation with GDA for 5 h or 73 h, 5·l of cells were plated at serial dilution (1:10 to 1:1000) on the agar medium YPD to estimate cell survival. The plated cells were incubated for 24 h at 37° C. and visually analyzed. The cells from the mature biofilm treated with water were used as a control. It was found that the GDA decreases cell viability of C. albicans and C. glabrata, particularly at high concentrations. At the concentrations of 0.2 and 0.5 g/ml after 5 h of incubation the cell viability was decreased by about 100 times for both C. albicans and C. glabrata. After 73 h of incubation with 0.5 g/ml of GDA the cell viability of C. albicans was decreased by about 1000 times (data not shown). C. glabrata proved to be more sensitive to GDA (FIG. 5).

Example 5—Microfluidics Study of Biofilm Development

Figure 6A:
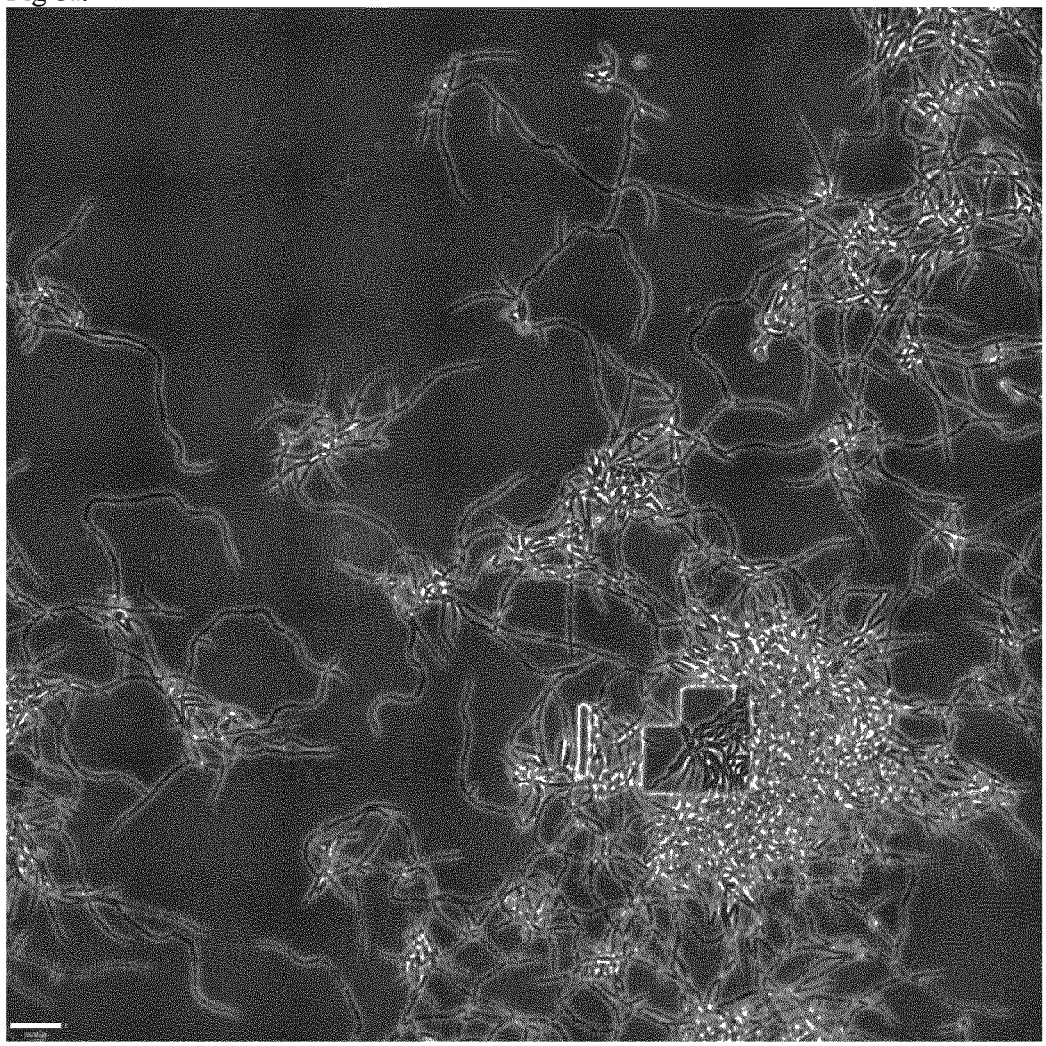
FIG. 6a shows microfluidics study of biofilm development of untreated *C. albicans* in minimal medium pH 7.0. The untreated cells mainly form hyphae.

To monitor the C. albicans cell morphology we studied the biofilm development also using microscopy and microfluidics. After the yeast cells were inoculated, hyphae started to form within first hour of incubation in the biofilm medium (YNB supplemented with 100 mM proline and 0.2% glucose, pH7.0). FIG. 6a shows untreated cells after 5 h. A pellet of GDA (2.5 g) was added to buffer solution of pH 3.71 (0.5 M $KH_2PO_4$/ortho phosphoric acid, 10 mL) at 37°

Figure 6B:
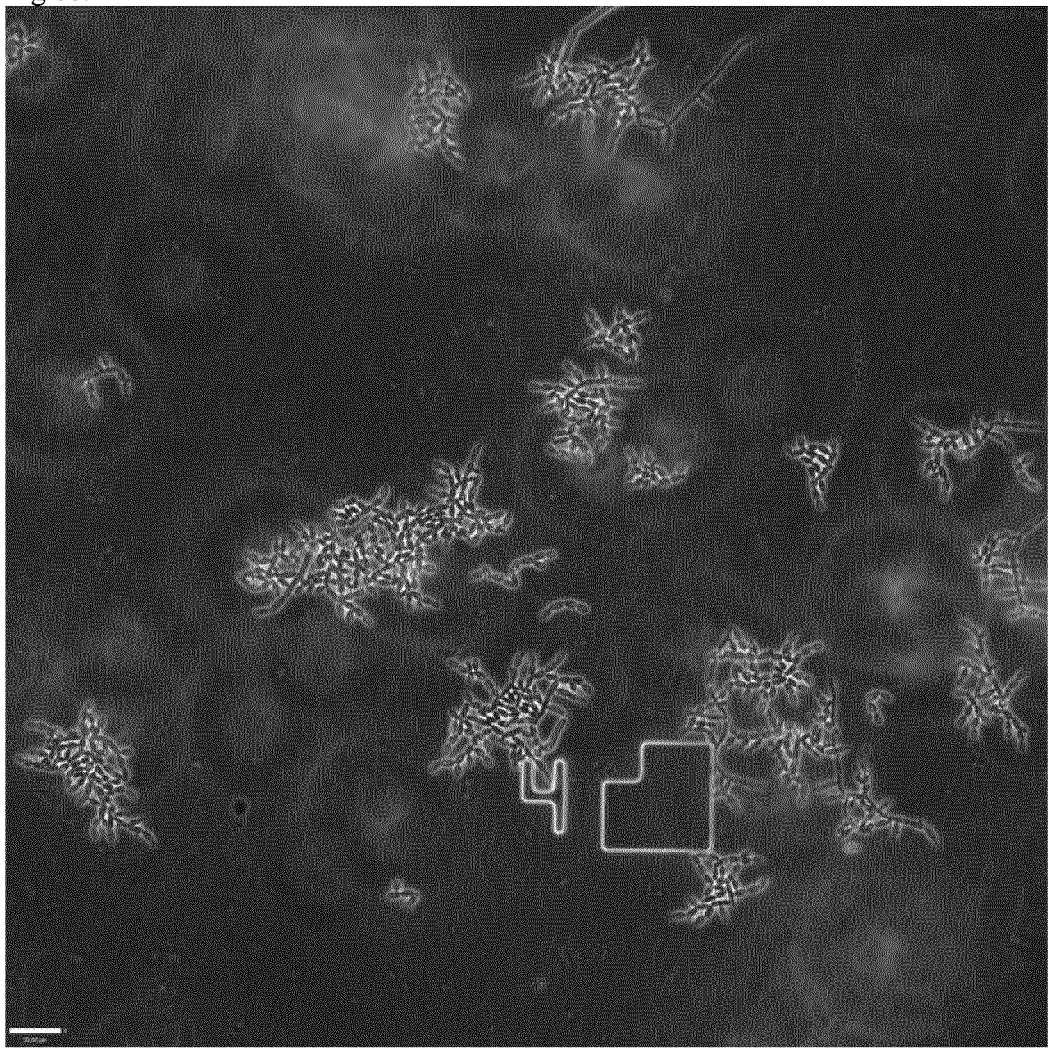
FIG. 6b shows microfluidics study of biofilm development of *C. albicans* treated in minimal medium with a hydrolysate of GDA at ×50 final concentration pH 3.8. The addition of GDA caused *C. albicans* to grow predominantly as yeast form, but not as hyphae.

C. A sample was taken after 1 h and diluted 50 times with biofilm medium and added to *C. albicans*. After 5 h most treated cells were planctonic (FIG. 6b).

Example 6—Viability of Different *Candida* Species in the Presence of GDA

Other *Candida* sp. studied were also sensitive (i.e. cell viability measure using the XTT assay, cf Example 4) to GDA. However, they displayed different levels of sensitivity. *Candida albicans* SC5314 displayed the lowest susceptibility and *Candida krusei* silicone isolate A4-1 displayed the highest susceptibility. The GDA-toxicity is mediated through cell wall damage as the cells exposed to GDA had lower viability on the medium with calcofluor white compared to that supplemented with osmotic stabilizer (0.5M sucrose) and compared to the untreated cells on these media. Table 3 summarizes qualitative effects shown by GDA.

TABLE 3

Sensitivity of different *Candida* species to GDA

| Strain | Sensitivity to GDA, 24 h exposure, plates |
|---|---|
| *C. albicans* SC5314 | + |
| *C. glabrata* CBS138 | ++++++ |
| *C. tropicalis* silicone isolate U3-3 | ++++++++ |
| *C. krusei* silicone isolate U3-5 | ++ |
| *C. tropicalis* silicone isolate A6-1 | +++ |
| *C. krusei* silicone isolate U2-12 | ++++++++ |
| *C. krusei* silicone isolate A5-2 | ++ |
| *C. krusei* silicone isolate A4-1 | +++++++++ |

To conclude, (i) GDA can break mature biofilm formed by *C. albicans* and *C. glabrata*, (ii) upon exposure to GDA, *C. albicans* transforms into yeast form, while the viability of *C. glabrata* decreases, (iii) the effect is clear even on other strains, i.e. *C. tropicalis* and *C. krusei*.

The invention claimed is:

1. A method for treatment of a fungal infection consisting of administration of a pharmaceutical formulation consisting of Glucono δ-lactone (formula (III)),

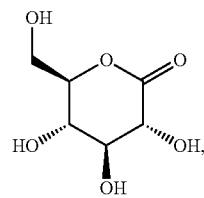

(III)

and one or more pharmaceutically acceptable excipients, to a subject in need thereof.

2. The method according to claim 1, wherein the fungal infection is a urogenital fungal infection or a vulvovaginal fungal infection.

3. The method according to claim 2, wherein the urogenital fungal infection or vulvovaginal fungal infection is vulvovaginal candidosis.

4. The method according to claim 3, wherein the vulvovaginal candidosis is caused by *Candida albicans, Candida glabrata, Candida krusei* and/or *Candida tropicalis*.

5. The method according to claim 1, wherein the glucono δ-lactone is present in an amount of 10 to 70 wt % of the formulation.

6. The method according to claim 1, wherein the pharmaceutical formulation comprises no more than 10 wt % water.

7. The method according to claim 1, wherein the pharmaceutically acceptable excipient is a carrier, a filler, and/or a buffering or pH-adjusting agent, or combination thereof.

8. The method according to claim 1, wherein the pharmaceutical formulation is formulated to release a compound according to formula (III) over an extended period of time or 4 hours or more after administration.

9. The method according to claim 1, wherein the pharmaceutical formulation is formulated as a tampon, vagitorium, vaginal aerosol, vaginal cup, vaginal gel, vaginal insert, vaginal patch, vaginal ring, vaginal sponge, vaginal suppository, vaginal cream, vaginal emulsion, vaginal foam, vaginal lotion, vaginal ointment, vaginal powder, vaginal shampoo, vaginal solution, vaginal spray, vaginal suspension, vaginal tablet, vaginal rod, vaginal disc, vaginal device, and any combination thereof, or wherein the pharmaceutical formulation is present on a sanitary article.

10. The method according to claim 9, wherein the pharmaceutical formulation is formulated as a vagitorium, vaginal insert, vaginal ring, vaginal suppository, vaginal tablet, vaginal rod, or vaginal disc.

11. The method according to claim 9 wherein the sanitary article is a tampon, a sanitary napkin, an incontinence pad or diaper, or a panty liner.

* * * * *